United States Patent

Grammenos et al.

Patent Number: 5,869,733
Date of Patent: Feb. 9, 1999

[54] PROCESS AND INTERMEDIATE PRODUCTS FOR PREPARING SUBSTANTIALLY ISOMER-PURE E-2(2-ARYLOXYMETHYLENE PHENYL)-CROTONIC ACID METHYL ESTERS

[75] Inventors: Wassilios Grammenos, Ludwigshafen; Norbert Götz, Worms; Hubert Sauter, Mannheim; Klaus Oberdorf, Heidelberg, all of Germany

[73] Assignee: BASF Aktiengesellschaft, Ludwigshafen, Germany

[21] Appl. No.: 930,942

[22] PCT Filed: Apr. 23, 1996

[86] PCT No.: PCT/EP96/01689

§ 371 Date: Oct. 9, 1997

§ 102(e) Date: Oct. 9, 1997

[87] PCT Pub. No.: WO96/34847

PCT Pub. Date: Nov. 7, 1996

[30] Foreign Application Priority Data

May 4, 1995 [DE] Germany ............ 195 16 407.5

[51] Int. Cl.⁶ ............... C07C 69/76; C07C 69/73
[52] U.S. Cl. ............... 560/8; 560/183
[58] Field of Search ................ 560/8, 183

[56] References Cited

U.S. PATENT DOCUMENTS

| 4,937,372 | 6/1990 | Wenderoth et al. | 560/55 |
| 5,298,527 | 3/1994 | Grammenos et al. | 514/539 |

FOREIGN PATENT DOCUMENTS

| 280 185 | 8/1988 | European Pat. Off. . |
| 513 580 | 11/1992 | European Pat. Off. . |

*Primary Examiner*—Gary Geist
*Assistant Examiner*—Rosalynd Keys
*Attorney, Agent, or Firm*—Keil & Weinkauf

[57] ABSTRACT

A process for the preparation of essentially isomerically pure methyl E-2-(2-aryloxymethylenephenyl)crotonates of the formula Ia

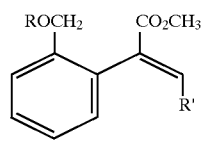

where R is an aromatic radical and R' is a $C_1$–$C_3$-alkyl group, which comprises first converting a suitable methyl 2-(2-aryloxymethylenephenyl)-α-ketoacetate with an alkyl metal compound of the formula III $$M\text{—}CH_2\text{—}R' \qquad \text{III}$$

where M is a metal ion equivalent into the corresponding methyl 2-(2-aryloxymethylenephenyl)-α-hydroxybutyrate of the formula IV, subsequently dehydrating IV in the presence of an acid to give a mixture of methyl E- and Z-2-(2-aryloxymethylenephenyl)crotonates and, subsequently, converting this mixture in the presence of a base in an inert polar solvent into the essentially isomerically pure methyl E-2-(2-aryloxymethylenephenyl) crotonate Ia.

9 Claims, No Drawings

PROCESS AND INTERMEDIATE PRODUCTS FOR PREPARING SUBSTANTIALLY ISOMER-PURE E-2(2-ARYLOXYMETHYLENE PHENYL)-CROTONIC ACID METHYL ESTERS

The present invention relates to a process for the preparation of essentially isomerically pure methyl E-2-[2-aryloxymethylenephenyl]crotonates of the formula Ia

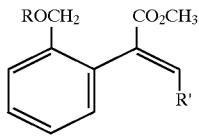

where R is an aromatic radical which is substituted by customary groups and R' is a $C_1$–$C_3$-alkyl group.

The literature discloses that methyl 2-[2-aryloxymethylenephenyl]crotonates are obtained from the corresponding methyl α-ketoacetates by a reaction similar to the method of Wittig or Wittig-Horner (EP-A 280 185, EP-A 513 580). No information is found in this literature on the preparation of the essentially pure E isomers which are preferred with regard to their biological properties.

The prior-art methods have the disadvantage that the triphenyl-phosphine oxide which is formed as a by-product necessitates a purification step which is difficult and complicated on an industrial scale.

It was therefore an object of the present invention to provide a process which yields the essentially pure E isomers of the methyl 2-[2-aryloxymethylenephenyl)crotonates. Moreover, it was an object of the present invention to provide an economical process for the preparation of these compounds which is simple to carry out on an industrial scale.

Accordingly, we have found that these objects are achieved by a process for the preparation of essentially isomerically pure methyl E-2-[2-aryloxymethylenephenyl] crotonates of the formula Ia which comprises first converting a suitable methyl 2-[2-aryloxymethylenephenyl]-α-ketoacetate of the formula II

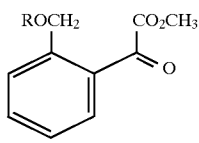

with an alkyl metal compound of the formula III

where M is a metal ion equivalent into the corresponding methyl 2-[2-aryloxymethylenephenyl]-α-hydroxybutyrate of the formula IV

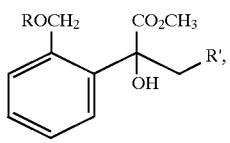

subsequently dehydrating IV in the presence of an acid to give a mixture of methyl E- and Z-2-[2-aryloxymethylenephenyl]crotonates of the formulae Ia and Ib

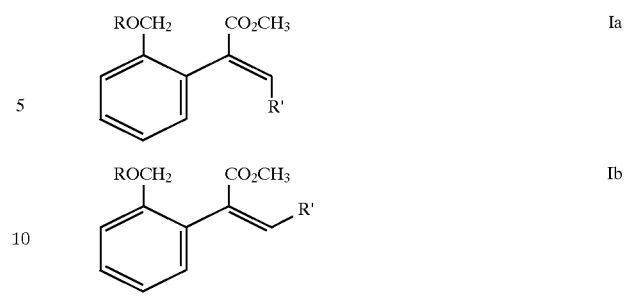

and, subsequently, converting this mixture in the presence of a base in an inert polar solvent into the essentially isomerically pure methyl E-2-[2-aryloxymethylenephenyl] crotonate Ia.

In the process according to the invention, the procedure is generally followed in which a suitable methyl 2-[2-aryloxymethylephenyl]-α-ketoacetate of the formula II is first converted with an alkyl metal compound of the formula III into the corresponding methyl 2-[2-aryloxymethylenephenyl]-α-hydroxybutyrate of the formula IV

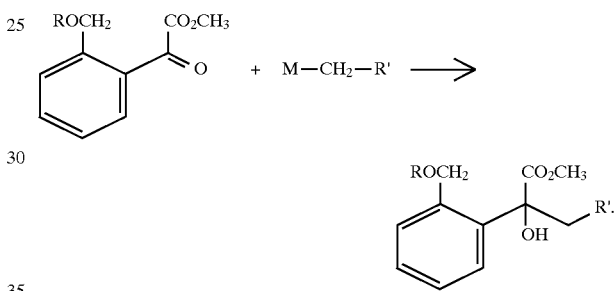

M in formula III is a metal ion equivalent. Suitable metal ions are, for example, ions of transition metals or of alkaline earth metals such as tin, magnesium, zinc, cadmium or mercury. Particularly preferred substances are alkyl tin halides, alkylmagnesium halides (for example ethylmagnesium chloride or ethylmagnesium bromide), ethylzinc chloride, ethylzinc bromide, ethylzinc iodide or diethylzinc.

This reaction is conventionally carried out at from –80° C. to 100° C., preferably –20° C. to 80° C.

Suitable solvents or diluents are aliphatic hydrocarbons such as pentane, hexane, cyclohexane and petroleum ether, aromatic hydrocarbons such as toluene, o-, m- and p-xylene, ethers such as diethyl ether, diisopropyl ether, tert-butyl methyl ether, dioxane, anisole and tetrahydrofuran, acetals such as formaldehyde dimethyl acetal and acetone dimethyl ketal, particularly preferably tetrahydrofuran, diethyl ether, diisopropyl ether, tertbutyl methyl ether, formaldehyde dimethyl acetal and acetone dimethyl ketal. Mixtures of the abovementioned solvents can also be used.

The alkyl metal compounds are generally employed in at least equimolar amounts. However, to increase the yield it is advantageous to employ the alkyl compounds III in an excess of from 500 mol % to 100 mol %, preferably 300 mol % to 150 mol %, especially 200 mol % to 100 mol %, based on the methyl 2-[2-aryloxymethylenephenyl]-α-ketoacetates of the formula II.

The reaction is advantageously carried out in such a way that the alkyl metal compound is taken up in a solvent or diluent and the resulting mixture is treated with the α-ketoester II, a little at a time, with cooling. After all of the ketoester II has been added, the reaction mixture is heated to approximately 25° C. (room temperature). The course of the reaction can be monitored chromatographically. After the reaction has ended, working-up of the reaction mixture is conventionally carried out in such a way that the mixture is first hydrolyzed with a dilute aqueous acid or water and subsequently extracted using an organic solvent.

The literature cited at the outset discloses the starting materials II which are required for the preparation of the compounds I. The alkyl metal compounds are also known (Houben-Weyl, Vol. 13/2, pp. 53 et seq. and pp. 570 et seq.) or can be prepared by following the literature cited.

The resulting methyl 2-[2-aryloxymethylenephenyl]-α-hydroxybutyrates of the formula IV can be converted, without further purification, into a mixture of the methyl E- and Z-2-[2-aryloxymethylenephenyl]crotonates of the formulae Ia and Ib by reacting them with an acid.

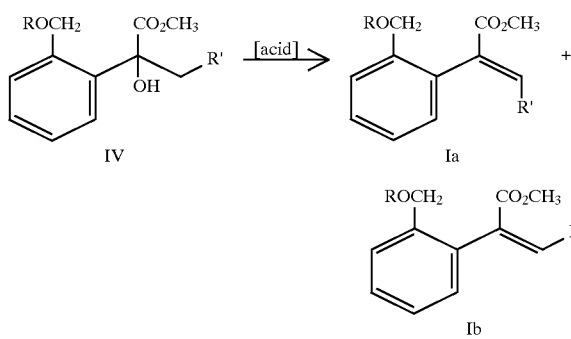

Suitable acids for the dehydration are generally all aprotic acids, ie. those acids which are capable of eliminating water from α-hydroxyesters, but these acids must not attack the benzyl ether group. Acids which have proven particularly advantageous are acids such as boron trifluoride, aluminum trichloride and iron(III) chloride, and, especially, acid halides such as phosgene, thionyl chloride, thionyl bromide, phosphorus trichloride, phosphorus tribromide, phosphorus oxychloride and sulfonyl halides.

The dehydration is conventionally carried out at from 0° C. to 230° C., preferably 20° C. to 150° C., in an inert organic solvent or diluent in the absence of water.

Suitable solvents or diluents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, with aromatic hydrocarbons being particularly preferred, esters such as adipic esters, acid amides such as dimethylformamide, N-methylpyrrolidone, tetramethylurea and dimethylpropyleneurea.

Mixtures of these may also be used.

The Lewis acids are generally used in at least equimolar amounts, in most cases, however, in an excess of from 100 mol % to 800 mol %, preferably 300 mol % to 600 mol %, based on the methyl 2-[2-aryl-oxymethylenephenyl]-α-hydroxybutyrates of the formula IV or, if desired, as solvents.

The reaction is advantageously carried out in such a manner that the α-ketoester is introduced at the reaction temperature either in bulk or in a solvent and the acid is subsequently added. The course of the reaction can be monitored chromatographically. After the reaction has ended, the reaction mixture is isomerized without further purification. Intermediates which arise [e.g. (2—ROCH$_2$—C$_6$H$_4$)—C(halo)(CO$_2$CH$_3$)—CH$_2$R'] can be converted into Ia and Ib in a similar manner by repeated treatment with the abovementioned acids.

The essentially isomerically pure methyl E-2-[2-aryloxymethylenephenyl]crotonates Ia can be obtained from the resulting mixture of methyl E- and Z-2-[2-aryloxymethylenephenyl]crotonates of the formulae Ia and Ib by reacting them with a base.

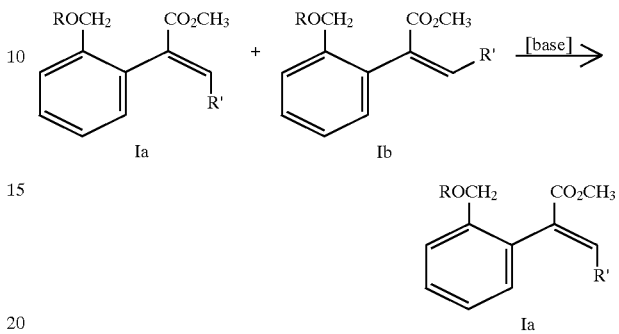

Bases which are suitable for the isomerization are bases such as alkaline earth metal carbonates such as lithium carbonate and calcium carbonate, and alkali metal hydrogen carbonates such as sodium hydrogen carbonate, alkali metal alcoholates and alkaline earth metal alcoholates such as sodium methanolate, sodium ethanolate and dimethoxymagnesium, and furthermore organic bases e.g. thiophenols, and amines such as dimethylamine, diethylamine, trimethylamine, triethylamine, triisopropylethylamine and N-methylpiperidine, pyridine, substituted pyridines, such as collidine, lutidine and 4-dimethylaminopyridine, and also bicyclic amines. Bases which have proven particularly advantageous are bases such as sodium methanolate, potassium methanolate, dimethylamine, diethylamine, dipropylamine, dibutylamine, pyridine, sodium thiomethylate, thiophenol and diphenyl sulfide.

The isomerization is conventionally carried out at from 0° C. to 180° C., preferably 20° C. to 160° C., in an inert organic solvent or diluent.

Suitable solvents or diluents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide and dimethylformamide, particularly preferably toluene, methylene chloride, diethyl ether, tert-butyl methyl ether, tetrahydrofuran, acetonitrile, methanol, ethanol, dimethyl sulfoxide and dimethylformamide.

Mixtures of these compounds can also be used.

The bases are generally employed in from catalytic amounts (for example 1 mol %) to equimolar amounts, preferably 1 mol % to 80 mol %, especially 1 mol % to 50 mol %, based on the mixture of Ia and Ib, or, if desired, they are used as solvents.

The reaction is expediently carried out in such a manner that the compounds Ia and Ib are taken up in a solvent or diluent and the resulting mixture is treated with base, a little at a time, at 20°–150° C. After all of the base has been added, the reaction mixture is left to stand at 20°–25° C. or at the reflux temperature of the solvent. The course of the reaction can be monitored chromatographically. After the reaction has ended, the reaction mixture is conventionally freed from solvent. The residue is then taken up in a solvent which is not miscible with water (for example ether and ethyl acetate) and washed using water and dilute aqueous acid.

A further important embodiment of the inventive process yields the essentially isomerically pure methyl E-2-[2-aryloxymethylenephenyl]crotonates Ia also by converting a methyl 2-[2-aryloxy-methylenephenyl]-α-hydroxybutyrate of the formula IV into the corresponding ester VI by reacting it with a compound V and subsequently eliminating VI to obtain Ia.

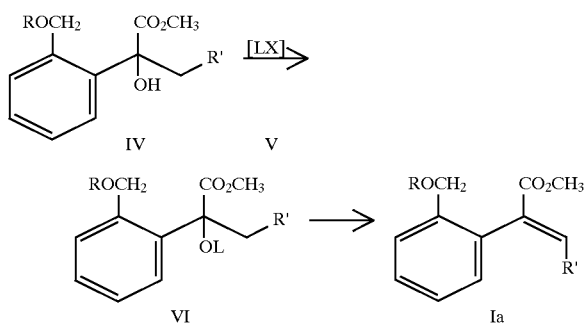

X in formula V is a halogen atom (e.g. chlorine, bromine or iodine) or a group LO; L in formulae V and VI is the radical of a leaving group, e.g. an aliphatic or aromatic sulfonyl group such as methylsulfonyl, trifluoromethylsulfonyl, phenylsulfonyl, 4-methylphenylsulfonyl or chloroformyl.

IV is esterified with V in a manner known per se at from 0° C. to 100° C., preferably 0° C. to 50° C., in an inert organic solvent in the presence of an acid or a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably aromatic hydrocarbons, ethers and dimethylformamide. Mixtures of these can also be used.

Suitable bases are generally inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, and also alkali metal alcoholates and alkaline earth metal alcoholates such as sodium methanolate, potassium methanolate, potassium tert-butanolate and dimethoxymagnesium, furthermore organic bases, e.g. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Sodium hydride, sodium methylate, triethylamine and pyridine are particularly preferred.

The bases are generally employed in catalytic amounts but they can also be used in equimolar amounts, in excess or, if desired, as solvents.

Substances which are used as acids and acidic catalysts are inorganic acids, such as hydrofluoric acid, Lewis acids such as boron trifluoride, aluminum trichloride, iron(III) chloride, tin(IV) chloride, titanium(IV) chloride and zinc(II) chloride.

The acids are generally employed in catalytic amounts but they can also be used in equimolar amounts, in excess or, if desired, as solvents.

The starting materials are generally reacted with each other in equimolar amounts. It may be advantageous for the yield to employ LX (V) in an excess based on IV.

The reaction mixtures are worked up in the customary manner, e.g. by mixing with water, separating the phases and, if desired, purifying the crude products by chromatography. Some of the intermediates and end products are obtained in the form of colorless or pale brown, viscous oils which are freed from volatile components or purified under reduced pressure at moderately elevated temperatures. If the intermediates and end products are obtained in the form of solids, they can also be purified by recrystallization or digestion.

The subsequent elimination of VI to obtain Ia is conventionally carried out at from 0° C. to 180° C., preferably 0° C. to 120° C., in an inert organic solvent in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, and also dimethyl sulfoxide and dimethylformamide, particularly preferably toluene, xylene, tetrahydrofuran, acetonitrile, dimethylformamide and dimethyl sulfoxide. Mixtures of these can also be used.

Suitable bases are, preferably, tertiary amines such as trimethylamine, triethylamine, triisopropylethylamine and N-methylpiperidine, pyridine, substituted pyridines such as collidine, lutidine and 4-dimethylaminopyridine, and also bicyclic amines. Triethylamine and pyridine are particularly preferred.

The bases are generally employed in catalytic amounts but they can also be used in equimolar amounts, in excess or, if desired, as solvents.

The starting materials are generally reacted with each other in equimolar amounts. It may be advantageous for the yield to employ the base in an excess or substoichiometric amount based on VI.

The elimination is advantageously carried out in such a way that the starting materials, in bulk or in a solvent, are treated with the base, a little at a time, at 20°–25° C. or with cooling. After all the base has been added, the reaction mixture is left to stand at this temperature or, if desired, heated. The course of the reaction can be monitored, chromatographically. After the reaction has ended, the reaction mixture is conventionally mixed with water. The product can be isolated from the organic phase and, if desired, further purified by chromatography.

Moreover, the esterification to obtain VI and elimination of VI to obtain Ia may also be carried out in one process step, without working up VI.

The process according to the invention is, in principle, suitable for preparing the compounds Ia disclosed in the literature. Accordingly, it is suitable for the preparation of essentially isomerically pure methyl E-2-[2-aryloxymethylenephenyl]crotonates of the formula Ia where the substituents have the following meanings:

R is an aromatic radical, in particular phenyl or heteroaryl, which is substituted by customary groups and can be partially or fully halogenated, and/or can have attached to it from one to three of the following groups: cyano, nitro, $C_1$–$C_4$-alkyl, $C_1$–$C_4$-haloalkyl, $C_1$–$C_4$-alkyloxy, $C_1$–$C_4$-haloalkyloxy, $C_1$–$C_4$-alkylthio, $C_1$–$C_4$-haloalkylthio, $C_3$–$C_8$-cycloalkyl, phenyl, phenoxy or benzyloxy, it being possible for the cyclic radicals, in turn, to be partially or fully hydrogenated and/or to have attached to them from one to three of the following groups: cyano, nitro, $C_1$–$C_4$-alkyl, $C_1$–$C_4$-haloalkyl, $C_1$–$C_4$-alkyloxy, $C_1$–$C_4$-haloalkyloxy, $C_1$–$C_4$-alkylthio, $C_1$–$C_4$-haloalkylthio, $C_3$–$C_8$-cycloalkyl, phenyl, phenoxy or benzyloxy, and/or can have attached to it a $CR^i$=$NOR^{ii}$ group where $R^i$ is hydrogen, cyano, halogen, $C_1$–$C_6$-alkyl, $C_1$–$C_6$-alkoxy, $C_1$–$C_6$-alkylthio, $C_3$–$C_6$-alkenyl, $C_3$–$C_6$-alkenyloxy, $C_3$–$C_6$-alkenylthio, $C_3$–$C_6$-alkynyl, $C_3$–$C_6$-alkynyloxy or $C_3$–$C_6$-alkynylthio, $C_3$–$C_6$-cycloalkyl, $C_3$–$C_6$-cycloalkyloxy, $C_3$–$C_6$-cycloalkylthio, aryl or heteroaryl and where $R^{ii}$ is hydrogen, $C_1$–C-alkyl, $C_3$–$C_{10}$-alkenyl or $C_3$–$C_{10}$-alkynyl, it being possible for these groups to be partially or fully halogenated and to have attached to them from one to three of the following radicals: cyano, nitro, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_3$–$C_6$-cycloalkoxy, aryl, aryloxy, heteroaryl or heteroaryloxy, it being possible for the cyclic radicals, in turn, to be partially or fully halogenated and/or to have attached to them from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino and di-$C_1$–$C_4$-alkylamino; and R' is $C_1$–$C_3$-alkyl, such as methyl, ethyl, propyl or 1-methylethyl, especially methyl.

The compounds Ia which are obtained by the process according to the invention are suitable for controlling animal or fungal pests.

PROCESS EXAMPLES

1. Preparation of the compounds of the general formula IV

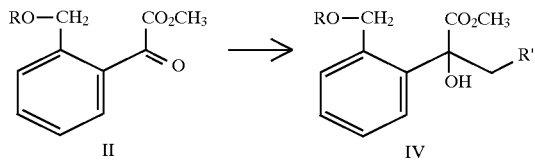

Example 1

[R=2,5-($CH_3$)$_2$-phenyl, R'=$CH_3$]

A solution of 300 g (2.2 mol) of zinc chloride in 1.9 l of tetrahydrofuran is added dropwise at 30° C. to an ethylmagnesium bromide solution prepared from 115 g (4.72 mol) of Mg filings and 516 g (4.72 mol) of ethyl bromide in 1.1 l of tetrahydrofuran, and stirring is continued for 2.5 hours at 25°–30°C. A solution of II [R=2,5-($CH_3$)$_2$-phenyl] in 1.25 l of tetrahydrofuran is added dropwise to this at -20 to 25° C.

in the course of 70 minutes, the cooling bath is removed, and stirring is continued for 16 hours at room temperature (RT). This reaction mixture is poured into a mixture of 3 kg of 20% strength hydrochloric acid and 3 kg of ice, extracted using 3 l of MtBE (=methyl tert-butyl ether), the phases are separated, and the aqueous phase is re-extracted using 1.6 l of MtBE. The combined organic phases are washed in succession using 2.4 l of water, 1.8 kg of saturated $NaHCO_3$ solution and 1 l of water and concentrated. This gives 626 g of IV as a viscous oil.

2. Preparation of the compounds of the general formula Ia and Ib

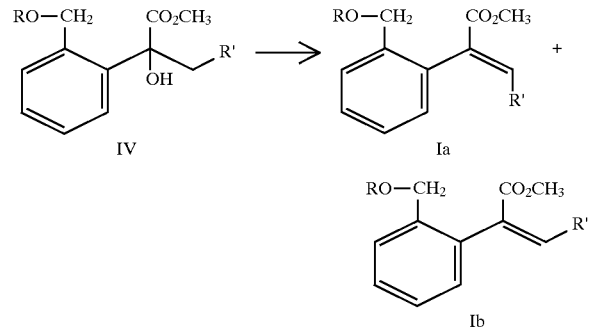

Example 2

[R=2,5-($CH_3$)$_2$-phenyl, R'=$CH_3$]

3.8 g (11.6 mmol) of the compound IV of Example 1 were introduced into 6.6 ml of dry pyridine. 6.6 ml of phosphorus oxychloride were carefully added dropwise with ice-cooling. The mixture was heated at 105° C., and stirring was continued at this temperature for 1 hour. After the mixture had cooled to room temperature, it was poured into ice-water and extracted using methylene chloride. The combined extracts were washed once using $NaHCO_3$ and twice using water, dried over sodium sulfate and concentrated. 3.3 g of Ia and Ib were obtained as the crude product in the form of an oil which was purified through silica gel using dichloroethane/cyclohexane 1:1 as the mobile phase.

Ia: $^1$H NMR (CDCl$_3$): δ=1.65 (d, 3H, $CH_3$), 2.21 (s, 3H, $CH_3$) 2.28 (s, 3H, $CH_3$), 3.79 (s, 3H, $OCH_3$), 4.87 (s, 2H, $CH_2$), 7.27 (9, 1H, CH), 6.6–7.6 (7H, ArH).

Ib: $^1$H NMR (CDCl$_3$): δ=2.18 (d, 3H, $CH_3$), 2.20 (s, 2H, $CH_3$), 2.27 (s, 3H, $CH_3$), 3.86 (s, 3H, $OCH_3$), 4.95 (s, 2H, $CH_2$), 6.25 (9, 1H, CH), 6.6–7.6 (7H, ArH).

Example 3

45 g (0.14 mol) of the compound IV of Example 1 are dissolved in 70 g of dimethyl adipate and 0.25 g of DMF (=dimethylformamide). Of this, 29 g are introduced into a reaction vessel and phosphene is passed in at an oilbath temperature of 100° C. and a condenser temperature of -20° C. (cryostat) until the internal temperature remains at 85° C. due to the phosgene reflux. At this temperature, the remaining solution is added dropwise from the top, and more phosgene is passed in. In total, 59 g of phosgene are passed in. Stirring is subsequently continued at this temperature for 10 hours, and nitrogen is passed through the solution for 1 hour. 11 g of dimethylformamide and 1.25 g of iron(III) chloride are then added under an argon atmosphere, the mixture is stirred for 15 hours at 140° C., a further 0.5 g of $FeCl_3$ is added, and the mixture is stirred for a further 4 hours at 140° C. According to GC, 63.1% of Ib and 29.1% of Ia are present, which can be isomerized without further purification.

Example 4

3.28 g of the compound IV of Example 1 are dissolved in 12 g of acetonitrile. 3.9 g of triethylamine and 0.43 g of lithium chloride are added. 2.1 g of p-toluenesulfonyl chloride are subsequently added, a little at a time, and the mixture is refluxed for 1 hour. After cooling, the mixture is partitioned between 40 ml of methylene chloride and 40 ml of 10% strength hydrochloric acid, and the organic phase is separated off, washed with 100 ml of saturated $NaHCO_3$ solution, dried over $Na_2SO_4$ and concentrated. This gives 2 g of product which contains 53.4% of Ib and 17.5% of Ia according to GC.

3. Preparation of the isomerically pure compounds Ia

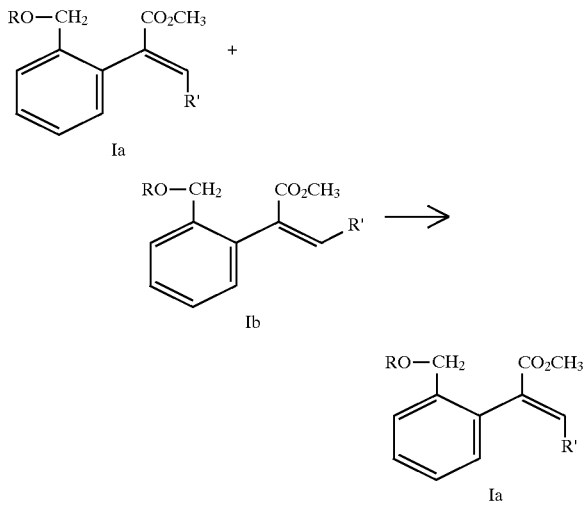

Example 5
[R=2,5-$(CH_3)_2$-phenyl, R'=$CH_3$]

10 g of a mixture of Ia (29%) and Ib (63.6%) are dissolved in 200 ml of tetrahydrofuran. 10 ml of 40% strength dimethylamine solution in water are added and the mixture is stirred under reflux for 20 hours. According to GC, the reaction solution contains 93% of Ia and 3% of Ib. For working up, the mixture is concentrated, taken up in ethyl acetate, washed with water, dried over $Na_2SO_4$ and reconcentrated. This gives 8.8 g of Ia as a colorless crystalline compound. The Ib isomer content is less than 2%.

Example 6
[R=2-$CH_3$-phenyl, R'=$CH_3$]

5 g of a mixture of Ia (40%) and Ib (55%) are dissolved in 100 ml of tetrahydrofuran. 10 mol % of sodium methylate in 40 ml of methanol are added and the mixture is stirred under reflux for 20 hours. Work-up is carried out as described in Example 5. This gives 4 g of product Ia (m.p. 46° C.). The Ib isomer content is less than 5%.

Example 7
[R=2-$CH_3$-phenyl, R'=$CH_3$]

30 g (0.101 mol) of a mixture of Ia (35%) and Ib (60%) in 500 ml of dimethylformamide are treated with 0.54 g of solid sodium methylate. The mixture is stirred for 12 hours at 130° C. and allowed to cool to room temperature, and the product is precipitated by adding ice-water. The product is then taken up in ethyl acetate, washed with water, dried over $Na_2SO_4$ and concentrated. This gives 28.6 g of product which contains less than 5% of Ib isomer and which crystallizes upon standing.

We claim:

1. A process for the preparation of essentially isomerically pure methyl E-2-[2-aryloxymethylenephenyl]crotonates of the formula Ia

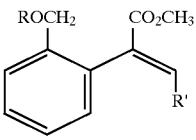

where R is an aromatic radical and R' is a $C_1$–$C_3$-alkyl group, which comprises first converting a suitable methyl 2-[2-aryloxymethylenephenyl]-α-ketoacetate of the formula II

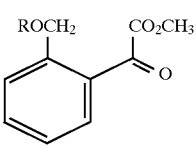

with an alkyl metal compound of the formula III

where M is a metal ion equivalent into the corresponding methyl 2-[2-aryloxymethylenephenyl]-α-hydroxybutyrate of the formula IV

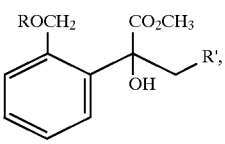

subsequently dehydrating IV in the presence of an acid to give a mixture of methyl E- and Z-2-[2-aryloxymethylenephenyl]crotonates of the formulae Ia and Ib

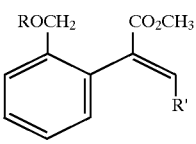

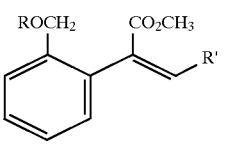

and, subsequently, converting this mixture in the presence of a base in an inert polar solvent into the essentially isomerically pure methyl E-2-[2-aryloxymethylenephenyl]crotonate Ia.

2. A process as claimed in claim 1, wherein II is reacted with III at from −80° C. to 100° C.

3. A process as claimed in claim 1, wherein the alkyl metal compound of the formula III used is an alkyl magnesium halide, an alkyl tin halide or dialkylzinc.

4. A process as claimed in claim 1, wherein the acid used is phosgene, thionyl chloride or sulfonyl chloride.

5. A process as claimed in claim 1, wherein IV is reacted to give a mixture of Ia and Ib at from 20° C. to 150° C.

6. A process as claimed in claim 1 wherein the mixture of Ia and Ib is isomerized to give essentially isomerically pure methyl E-2-[2-aryloxymethylenephenyl]crotonate Ia in the presence of an amine.

7. A process as claimed in claim 1, wherein the mixture of Ia and Ib is isomerized to give essentially isomerically pure methyl E-2-[2-aryloxymethylenephenyl]crotonate Ia in the presence of an organic sulfide or disulfide.

8. A process as claimed in claim 1, wherein the mixture of Ia and Ib is isomerized to give essentially isomerically pure methyl E-2-[2-aryloxymethylenephenyl]crotonate Ia in the presence of an alcoholate.

9. A methyl 2-[2-aryloxymethylenephenyl]-$\alpha$-hydroxybutyrate of the formula IV as claimed in claim 1.

* * * * *